United States Patent
Yamada et al.

(10) Patent No.: US 10,481,002 B2
(45) Date of Patent: Nov. 19, 2019

(54) SYSTEMS AND METHODS FOR SELF-REFERENCED DETECTION AND IMAGING OF SAMPLE ARRAYS

(71) Applicant: GENERAL ELECTRIC COMPANY, Schenectady, NY (US)

(72) Inventors: Masako Yamada, Niskayuna, NY (US); Sandip Maity, Bangalore (IN); Sameer Dinkar Vartak, Bangalore (IN); Rajesh Langoju, Bangalore (IN); Abhijit Patil, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 28 days.

(21) Appl. No.: 14/342,811

(22) PCT Filed: Sep. 28, 2012

(86) PCT No.: PCT/SE2012/051037
§ 371 (c)(1),
(2) Date: Mar. 5, 2014

(87) PCT Pub. No.: WO2013/048328
PCT Pub. Date: Apr. 4, 2013

(65) Prior Publication Data
US 2014/0249055 A1    Sep. 4, 2014

(30) Foreign Application Priority Data
Sep. 30, 2011    (IN) .......................... 3391/CHE/2011

(51) Int. Cl.
*G01N 21/45*    (2006.01)
*G01J 3/28*    (2006.01)
(Continued)

(52) U.S. Cl.
CPC .......... *G01J 3/2823* (2013.01); *G01N 21/253* (2013.01); *G01N 21/45* (2013.01);
(Continued)

(58) Field of Classification Search
CPC ..... G01J 3/2823; G01N 21/253; G01N 21/45; G01N 21/55
See application file for complete search history.

(56) References Cited

U.S. PATENT DOCUMENTS 6,493,097 B1 * 12/2002 Ivarsson ............ G01B 11/0625
356/630
7,233,396 B1    6/2007 Hall et al.
(Continued)

FOREIGN PATENT DOCUMENTS

| EP | 1643237 | 4/2006 |
|---|---|---|
| EP | 2221603 | 8/2010 |
| WO | 2009/013707 A2 | 1/2009 |

OTHER PUBLICATIONS

European Search Report for related European Application No. 12836873.5 dated Apr. 24, 2015.
(Continued)

*Primary Examiner* — Melanie Brown
(74) *Attorney, Agent, or Firm* — Arent Fox, LLP

(57) ABSTRACT

A system for detecting an array of samples having detectable samples and at least one reference sample is provided. The system comprises an electromagnetic radiation source, a sensing surface comprising a plurality of sample fields, wherein the plurality of sample fields comprise at least one reference field, a phase difference generator configured to introduce differences in pathlengths of one or more samples in the array of samples, and an imaging spectrometer configured to image one or more samples in the array of samples.

11 Claims, 7 Drawing Sheets

(51) Int. Cl.
*G01N 21/25* (2006.01)
*G01N 21/55* (2014.01)
*G01N 21/552* (2014.01)

(52) U.S. Cl.
CPC ........... *G01N 21/55* (2013.01); *G01N 21/553* (2013.01); *G01N 21/554* (2013.01)

(56) References Cited

U.S. PATENT DOCUMENTS

| | | | | |
|---|---|---|---|---|
| 2004/0081384 A1* | 4/2004 | Datesman | ........ | G01N 33/54373 385/12 |
| 2004/0100636 A1* | 5/2004 | Somekh | ............ | G01N 21/6458 356/497 |
| 2005/0052655 A1 | 3/2005 | Jones et al. | | |
| 2006/0017931 A1* | 1/2006 | Kimura | ................ | G01N 21/553 356/445 |
| 2006/0146333 A1 | 7/2006 | Hakamata et al. | | |
| 2006/0256343 A1* | 11/2006 | Choma | ............. | G01B 9/02083 356/450 |
| 2007/0009935 A1* | 1/2007 | Joo | .................... | G01B 11/0625 435/6.12 |
| 2007/0065954 A1 | 3/2007 | Taya et al. | | |
| 2008/0002202 A1* | 1/2008 | Hall | ....................... | G01N 21/21 356/369 |
| 2008/0153105 A1* | 6/2008 | Martin | ................... | G01N 21/84 435/7.1 |
| 2009/0011948 A1* | 1/2009 | Unlu | ..................... | G02B 21/34 506/9 |
| 2011/0122412 A1* | 5/2011 | Joo | ........................ | G01N 21/53 356/451 |
| 2012/0019834 A1* | 1/2012 | Bornhop | ................ | G01N 21/45 356/517 |
| 2012/0214707 A1* | 8/2012 | Ymeti | .................... | G01N 21/45 506/9 |

OTHER PUBLICATIONS

Sims, M.R. et al. "The specific molecular identification of life experiment (SMILE)." Planetary and Space Science, 2005, pp. 781-791, vol. 53-No. 8, Elsevier Ltd.
PCT/SE2012/051037 ISRWO dated Feb. 25, 2013.
Sims et al., "The Specific Molecular Identification of Life Experiment (SMILE)," Planetary and Space Science, 2005, 53:781-791.
English Translation of the Office Action issued by the State Intellectual Property Office for Chinese Application No. 201280047609.3 dated Aug. 25, 2015 (12 pages).

* cited by examiner

SYSTEMS AND METHODS FOR SELF-REFERENCED DETECTION AND IMAGING OF SAMPLE ARRAYS

This application is a filing under 35 U.S.C. 371 of international application number PCT/SE2012/051037, filed Sep. 28, 2012, which claims priority to India application number 339/CHE/2011 filed Sep. 30, 2011, the entire disclosure of which is hereby incorporated by reference.

BACKGROUND

The invention relates to detection and imaging, and more particularly to systems and methods for optical detection and imaging of sample arrays.

Surface plasmon resonance (SPR) detection is an optical detection technique that is used to detect molecular adsorptions and interactions. The SPR detection is used in a wide variety of chemical systems, including biosensors. Typically, SPR sensors comprise an arrangement where a prism supports a thin metal layer. A ligand molecule is immobilized on one side of the thin metal layer to form a modified metal surface from the thin metal layer. A sample is disposed on the modified metal surface. A light beam incident on the sample excites surface plasmons in the thin metal layer in a resonant manner. The surface plasmons propagate in a direction parallel to the interface formed between the thin metal layer and the prism (metal/prism interface). Since the surface plasmons are present at the boundary of the thin metal layer and an external medium (e.g., air or water), the oscillations of the surface plasmons are responsive to any changes in the boundary of the metal and the external medium, such as the adsorption of molecules on the metal surface. SPR phenomenon is typically detected by sensing refractive index changes near the surface of the thin metal layer. A reflection spectrum of the modified metal surface may be determined by measuring the intensity of a reflected light as a function of an angle of incidence or a wavelength of the incident light. The sensitivity of the SPR phenomenon towards refractive index changes at the boundary is useful in observing and quantifying chemical reactions at a thin metal film/sample solution interface.

Typically, SPR systems use two different paths in an interferometer. A first path may be referred to as a reference arm and a second path may be referred to as a sample arm. The general direction from a radiation source towards a reference is referred to as a reference arm, and a general direction from the radiation source towards the sample is referred to as a sample arm. The incident light from the radiation source is split into two portions, a first portion travels through the reference arm and is incident on the reference sample, and the second portion travels through the sample path and is incident on the samples. Having two different paths in the interferometer makes the system susceptible to environmental factors, such as vibrations, resulting in noise in the detection and imaging. The SPR techniques in an interferometer configuration are relatively more sensitive to environmental factors such as vibrations and temperature fluctuations. The vibrations may cause misalignment between the two arms in the interferometer, which may result in lack in coherency of the light travelling through the two different paths, thus, affecting the sensitivity of the detection.

Therefore, it is desirable to have improved systems and methods for detecting and imaging of arrays of samples.

BRIEF DESCRIPTION

In one embodiment, a system for detecting an array of samples having detectable samples and at least one reference sample is provided. The system comprises an electromagnetic radiation source, a sensing surface comprising a plurality of sample fields, wherein the plurality of sample fields comprise at least one reference field, a phase difference generator configured to introduce differences in pathlengths of one or more samples in the array of samples, and an imaging spectrometer configured to image one or more samples in the array of samples.

In another embodiment, a detection and imaging system for detecting and imaging an array of samples is provided. The system comprises a broadband light source configured to illuminate the array of samples, an optical engine, an image acquisition unit configured to acquire image data, and a signal processing unit for processing the acquired image data. The optical engine comprises a SPR sensing surface having sample fields and at least one reference field, a phase difference generator configured to introduce differences in pathlengths of one or more samples in the array of samples, an image acquisition unit configured to acquire image data, and a signal processing unit for processing the acquired image data.

In one example, a method for s imaging of samples in an array is provided. The method comprises providing an incident radiation, illuminating the samples in the array of samples with the incident radiation to produce resultant beams, wherein the array of samples comprise a reference sample, introducing a path difference in one or more of the samples of the array of samples, interfering a resultant reference beam with resultant sample beams to form interference spectra, acquiring the interference spectra, and reconstructing spectral characteristics of the one or more samples.

DRAWINGS

These and other features, aspects, and advantages of the invention will become better understood when the following detailed description is read with reference to the accompanying drawings in which like characters represent like parts throughout the drawings, wherein.

DETAILED DESCRIPTION

Systems and methods for self-referenced detection and imaging of samples are provided. The systems and methods may be configured for simultaneous detection of a plurality of samples. The samples may be disposed in a one-dimensional (1D) or a two dimensional (2D) array. The samples may be disposed in their respective sample fields on a sensing surface. One or more sample fields may be configured to receive reference samples. Alternatively, one or more sample fields may be configured to act as reference samples. In certain embodiments, the simultaneous detection may comprise detecting the samples in a single shot or frame. The systems and methods may be suitable for a high throughput detection and imaging of samples. In one embodiment, the image of spectral characteristics of a plurality of samples may be reconstructed by introducing a spectral separation in the array of samples in a first direction (e.g., x-direction), and imaging the array of samples in a second direction (e.g., y-direction), where the second direction is different from the first direction.

In certain embodiments, a self-referenced detection system for an array of samples comprising detectable samples and at least one reference sample is provided. Throughout the application, the combination of detectable and reference samples may be referred to as "samples". The samples that are to be detected may be referred to as "detectable samples". In one example, detection may comprise determining spectral characteristics of the detectable samples. The reference samples may be configured for providing referencing for detection of spectral characteristics of the detectable samples. The system comprises an electromagnetic radiation source, a sensing surface comprising a plurality of sample fields, wherein at least one of the sample fields of the plurality of sample fields is a reference field. The system may further comprise a phase difference generator configured to introduce differences in pathlengths of one or more samples in the array of samples, and an imaging spectrometer configured to image one or more samples in the array of samples.

Figure 1:
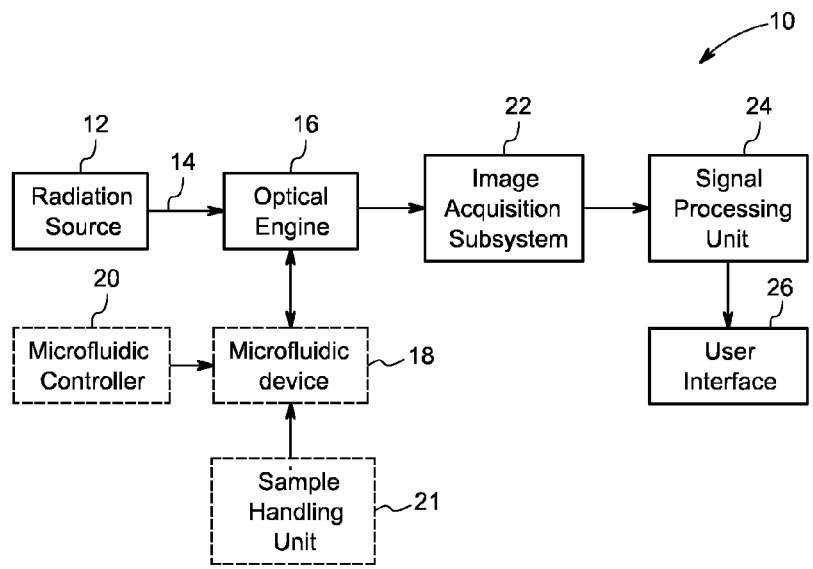
FIG. 1 is a block diagram of an example self-referencing detection and imaging system for simultaneous detection of an array of samples.

FIG. 1 illustrates a self-referenced detecting and imaging system 10 for simultaneously detecting two or more samples in an array of samples. The system 10 comprises an electromagnetic radiation source 12 for irradiating the array of samples with electromagnetic radiation 14. The electromagnetic radiation source 12 may produce visible light, or near infrared light depending on the types of samples to be detected. Non-limiting examples of the radiation source 12 may comprise a light emitting diode, super luminescent light emitting diode, broadband light source, or a combination thereof. The broadband light source may emit a continuous spectrum output over a range of wavelengths at any given point in time. The broadband light source may include sources such as but not limited to, a tungsten lamp, white light source, xenon lamp, metal halide lamp, phosphor source, or a combination thereof.

The radiation 14 from the radiation source 12 may be directed to an optical engine 16. The optical engine 16 comprises an optical arrangement for directing the radiation 14 to a sensing surface (not shown). The sensing surface may form a part of the optical engine 16. The system 10 comprises a common optical path for reference and detectable samples. The common optical path serves as both reference and sample path and may be used for providing referencing for the samples. The incident radiation comprising beamlets for illuminating the reference samples and detectable samples traverse a common optical path to illuminate the samples. The incident beamlets for reference samples and the incident beamlets for the detectable samples travel in the same direction, which is from the radiation source 12 to the sensing surface. The resultant radiation from the samples comprising resultant beamlets from the reference samples and detectable samples traverse a common optical path to reach a detector. The incident beamlets for reference samples and the incident beamlets from the detectable samples travel in the same direction, which is from the sensing surface to the detector. The system 10 is configured to provide referencing of the samples 30 without a need for separate optical paths for reference and detectable samples. Self-referencing eliminates a need for a reference arm. This capability of the system 10 of being able to provide self-referencing minimizes or eliminates noise that may be otherwise introduced when two different optical paths are used in an interferometer system, such as the system 10. The self-referencing may be provided by one or more reference samples disposed on the sensing surface.

The sensing surface may comprise a plurality of sample fields for disposing the samples. The sample fields may comprise one or more detectable samples and at least one reference sample. The sample fields may be disposed on the sensing surface as a 1D or 2D array. The samples may be disposed in some or all of the sample fields. The sample fields to dispose the samples may be chosen in a determined geometrical pattern. Alternatively, the sample fields may be chosen in an irregular fashion to dispose the samples. One or more sample fields may comprise the reference samples, two or more sample fields may comprise detectable samples. Any sample field in the array of sample fields may be chosen to receive the reference samples. The sample fields configured to receive the reference samples may be referred to as "reference fields" or "reference sample fields".

In certain embodiments, the reference sample may comprise a material with determined or known spectral absorption values. The known spectral absorption values may comprise a known constant value or a known time varying value. In a case of a SPR system, a material of the reference sample may be such that the SPR phenomenon falls outside the detectable range of the surface of the reference field. The material may be a high or low refractive index material for which the SPR phenomenon falls outside the detectable range of the surface of the reference field. The detectable range refers to a range of refractive indices within which SPR phenomenon may be realized in the system. In one example, the detectable range of the system may be in a range from about to about 1.32-1.41. In this case, a low refractive index material may refer to a material comprising a refractive index of below 1.32, and a high refractive index material may refer to a material comprising a refractive index of 1.41 and above. In examples where the reference field comprises a SPR metal film, the reference field may comprise a solution with known spectral absorption. In these embodiments, the interference spectra may be processed to account for the known spectral absorption value.

In certain other embodiments, the reference fields may be configured to reflect the incident radiation. In these embodiments, the reference fields may not comprise a reference sample, the reference fields themselves may serve as a reference sample, or air may serve as the reference sample.

In one embodiment, one of the sample fields from the plurality of sample fields may be selected as a reference field, and no further modification may be provided to the sample field and no sample may be disposed in this sample field. In this example, a sample field having air present in the system may be used as a reference field.

In one embodiment, the reference field configured to act as a reference sample may comprise one or more layers or coatings of a material with known spectral absorption value. The materials for layers or coatings may be a high or low refractive index material having refractive index outside the detectable range of the system. Non-limiting examples of materials that may be present in the reference field in the form of a layer or a coating may comprise dielectric oxides (e.g., silicon dioxide), zinc sulphide, porous silicon, gold, silver, aluminum, and other suitable high or low refractive index materials.

In a case of total internal reflection based detection techniques, such as but not limited to SPR, the reference field may comprise glass with air, or glass with a material with known spectral absorption. The material with known spectral absorption may be a high or low refractive index material. In one embodiment, the material may be in the form of a solution. The reference field may comprise conventional reference solutions. In one embodiment, the material may be in the form of one or more layers or coatings. In this embodiment, the location of the reference field may be masked while depositing the SPR metal film (e.g., gold film). In a case of about normal incidence of incident radiation on the sensing surface, the reference fields may comprise a multilayer dielectric structure, or a material with known or about zero spectral absorption.

In one embodiment, the reference sample may be a non-absorptive sample. That is, the reference sample may comprise a material that reflects major portion of the incident radiation. In the case of SPR systems, the reference sample may itself exhibit minimal or zero surface plasmon resonance (SPR) phenomenon.

In certain embodiments, one or more sample fields configured to receive detectable samples may be functionalized. In these embodiments, the sample fields may be immobilized with functionalizing material, such as ligand molecules.

A microfluidic device 18, such as a microfluidic chip, may be operatively coupled to the sensing surface to provide samples to the sensing surface. The microfluidic device 18 may be configured to provide the samples to the corresponding sample fields on the sensing surface. In embodiments where a reference sample needs to be disposed in reference fields, the microfluidic chip may provide reference and active samples to the reference and sample fields, respectively. A microfluidic controller 20 may be provided to control the microfluidic operations of the microfluidic device 18. Optionally, a sample handling unit 21 may be operatively coupled to the microfluidic chop 18. The sample handling unit 21 may be coupled to fluid ports of the microfluidic device 18 for transporting samples to and from the microfluidic device 18, or for carrying off waste flows from the microfluidic device 18. The sample handling unit 21 may comprise chambers or reagent reservoirs for storing sample solution, flow through port for transporting samples, a pumping device, and a sample flow controller. The sample handling unit 21 may be configured to modify the transport of samples based on the detection of samples by the system 10. The sample handling unit 21 may be configured to accommodate a variety of samples including liquid and gaseous samples. The sample handling unit 21 may comprise provisions for sample preparation and processing, such as but not limited, metering, mixing and diluting. The sample handling unit 21 may comprise a thermal element for heating or cooling the samples.

In certain embodiments, a phase difference or a path length difference may be introduced in the incident radiation or in the resultant radiation. The phase difference may be introduced using a phase difference generator as described in detail in the commonly assigned U.S. patent application Ser. No. 12/914,622 titled "Systems and methods for detection and imaging of two-dimensional sample arrays". The phase difference may be introduced in the incident radiation by disposing the phase difference generator between an excitation source and the sensing surface. The phase difference may be introduced in the resultant radiation by disposing the phase difference generator between the sensing surface and detector. The phase difference may be introduced in a direction other than an imaging direction. The phase difference may be used in spectral separation of the samples in the direction in which the phase difference is introduced. The phase difference may be introduced in the incident radiation 14 or a resultant reflected radiation in a first direction. As a result, the resultant reflected beams from the sample fields in the first direction may be phase separated. It should be noted that the resultant reflected radiation comprise beams reflected from the reference samples and active samples.

In a case of a 1D array of samples, the phase difference may be introduced in each of the samples in the 1D array of samples. The reference sample may be disposed in one of the sample fields of the 1D array. In one example, one or more samples fields may be combined; the combined sample fields may be used as a reference field.

In a case of a 2D array of samples comprising a plurality of rows and columns, there may be one or more reference samples. In one example, each row of the samples may comprise a reference sample of its own. In this example, the phase difference may be introduced in each element of a row. The reference sample of each row may be disposed in that particular row. In one example, the reference sample may be symmetrically positioned with respect to other samples in the row. The position of the reference sample in the different rows may be same or different. In one example, traversing in the x-direction, the first samples fields in each row may comprise a reference sample. In another example, one or more reference samples may be positioned at difference locations in the various rows.

The samples may be detected by analyzing interference spectra formed by interference of phase differenced sample beams with the reference beam. The interference spectrum from the optical engine 16 is received by the image acquisition unit 22. The image acquisition unit 22 acquires image data that includes interference in spectral domain. The image acquisition unit 22 may include a combination of a detector and a grating. In one embodiment, the grating comprises 3600 lines per mm, however, other values of grating lines per mm may also be selected. In one embodiment, the grating may be tilted at a determined angle to obtain additional spatial separation of frequencies. In one embodiment, the phase difference may be introduced in the x-direction and the imaging may be performed in the y-direction.

The image acquisition unit 22 may include additional optical elements such as lens for collimating or focusing the radiation. The acquired image may be processed using a signal processing unit 24. A graphical user interface (GUI) 26 may be used to provide a user interface to allow the user to interact with the detection system 10.

The signal processing unit 24 may comprise a microprocessor, microcontroller and a digital signal processor (DSP). The system 10 may also comprise a storage device (not shown) for at least temporarily storing one or more images. The storage device may comprise, but is not limited to, any suitable hard drive memory associated with the processor such as the ROM (read only memory), RAM (random access memory) or DRAM (dynamic random access memory) of a CPU (central processing unit), or any suitable disk drive memory device such as a DVD or CD, or a zip drive or memory card. The storage device may be remotely located from the signal processing unit 24 or the imaging device, and yet still be accessed through any suitable connection device or communications network including but not limited to local area networks, cable networks, satellite networks, and the Internet, regardless whether hard wired or wireless.

Figure 2:
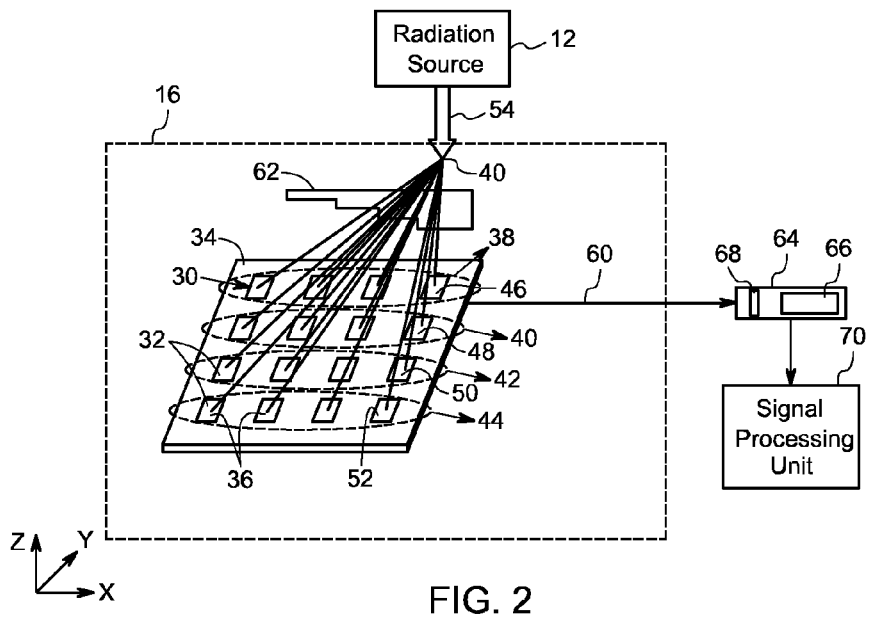
FIG. 2 is a schematic drawing of an example of an optical engine of FIG. 1.

FIG. 2 illustrates an example of the optical arrangement within the optical engine 16. The optical engine 16 comprises an optical arrangement for directing a portion of the radiation 14 from the radiation source 12 to an array 30 of samples 32. One or more samples 32 in the array 30 may be reference samples. The samples 32 may be chemical or biological samples. In one embodiment, the samples 32 may be chemically or biologically active samples. The chemically or biologically active samples 32 may produce a determined response when they come in contact with a chemical or a biological entity, respectively. In one example, the samples 32 may have a time constant optical property. The samples 32 may comprise optically active materials. In one example, the samples 32 may be able to absorb, transmit, or reflect the incident radiation.

The sample array 30 may be disposed on a sensing surface 34. The sensing surface 34 may comprise a plurality of sample fields 36 that contain the samples 32. The array 30 may be of varying sizes such as, but not limited to, a 4×4 array, a 6×6 array, or an 8×8 array of samples 32. In a case of a 2D array, each row of the array 30 may comprise a corresponding reference sample. The reference sample for a row may be disposed in one of the sample fields of that row. For example, rows 38, 40, 42 and 44 may comprise reference samples at sample locations represented by reference numerals 46, 48, 50 and 52, respectively. Although illustrated as a 2D array, in an alternate embodiment, the sample array may be a linear array. In a case of a 1D array, one sample field may be selected as a reference field. The positions of the different samples may vary from one row to another. For example, traversing in x-direction, the first sample of row 33 may be the reference sample, whereas the row 35 may have a second sample as a reference sample, and so on.

In certain embodiments, providing a common optical path for detectable and reference samples by disposing the detectable and reference samples on the same sensing surface 34 may enhance the sensitivity of the overall detection and imaging system by reducing the noise in the measurements. For example, disposing the reference samples and detectable samples on the same sensing surface 34, may nullify any undesirable noises caused by vibrations or temperature fluctuations.

The sensing surface 34 may be a spectrally modifying surface that may reflect, absorb, or transmit at least a portion of the incident sample beam 54. The sensing surface 34 may be selected based on the particular detection techniques that are being used. Non-limiting examples of the detection techniques may include surface plasmon resonance (SPR) such as but not limited to, a localized SPR (LSPR), nano-grating SPR, label-free SPR, or other techniques such as but not limited to reflectometric interference spectroscopy (RIfS). In case of LSPR, the sensing surface 34 may include a transmitting substrate. Metal structures may be disposed on the transmitting substrate. In case of RifS the sensing surface 34 may include a transmitting substrate. In case of nano-grating SPR, the sensing surface 34 may comprise a transmitting substrate having nano gratings disposed on one side of the transmitting substrate.

The sample fields 36 may be formed on the sensing surface 34 by processing corresponding portions of the sensing surface 34. The processing may comprise fabrication techniques such as but not limited to, etching, patterning, or functionalizing at least portions of the sensing surface 34 corresponding to the sample fields 36. In one embodiment, portions of a top index layer of the sensing surface may be etched to form trenches for forming the sample fields 36. In the case of SPR detection, the sample fields 36 may be coated with a thin metal film, such as but not limited to, gold or silver, to enable SPR when the sample fields are irradiated with excitation radiation. In one example, the thin metal film may have a thickness in a range from about 0.001 microns to about 1 micron to provide for the SPR. The volume of the sample fields may be sufficient for the detection of volumes of chemical or biological agents as low as micro-liters, or pico-liters.

In certain embodiments, the sample fields 36 on the sensing surface 34 may be functionalized with one or more functional agents. The functional agents may comprise a coating of specific antibodies, proteins, DNA sequences, ligand molecules or amino acid sequences that are sensitive and specific to chemical or biological agents of interest. The functional agents may be present in the form of a layer or a coating, also referred to as a functionalized coating. By changing the functional agents the systems and methods may be used for linear detection or threshold detection of predetermined agents. In one embodiment, the detection may be based on the competitive binding of the sample to the binding sites of the ligand. Same or different ligands may be disposed in the different sample fields 36 of the sample array 30. The functional agents may be disposed in discrete areas of the sensing surface 34. These discrete areas may correspond to the sample fields 36. Thus, the functional agents may be present in the form of an array of discrete sample-binding regions. The different sample fields 36 may comprise same or different functional agents. For example, one or more of the sample fields 36 may comprise a ligand molecule different than the other sample fields. In one embodiment, all the different sample fields 36 may comprise different ligand molecules. The ligands may comprise one or more of a biopolymer, an antigen, antibody, nucleic acids and hormone ligands. In one example, for antibody binding measurements, an antigen may be immobilized on the sample fields 36 and the sensing surface may be exposed to a solution containing the antibody of interest, and binding proceeds.

The functionalizing material may saturate due to high concentrations of the samples in the array 30, or due to exposure of the sensing surface 34 to the sample solution for a long period time. In a case the functionalizing material is saturated, the corresponding sample field 36 or the sensing surface 34 needs to be regenerated to continue the detection. In one embodiment, the sensing surface 34 may be regenerated to allow the detection system to be used over and over again, thereby reducing the working material required, with a consequent significant cost reduction. In one example, the regeneration of the sensing surface 34 may be achieved by applying a different solution than previously used. In one example, the sensing surface 34 may be exposed to a base solution, such as sodium hydroxide, or to an acidic solution, such as, glycine hydrogen chloride buffer having pH 2.0, to regenerate the sensing surface. The regeneration of the ligands considerably reduces the cost of the sensor assembly. In one embodiment, regeneration of the ligands enables detection of different sample solutions. In this embodiment, the ligands are regenerated after detecting existing sample solution in a sample field, and before providing the next sample solution in the sample field.

In one embodiment, a plurality of flow cells of a microfluidic device (not shown) may be operatively coupled to the sensing surface 34 to provide the samples 32 to the one or more sample fields 36 on the sensing surface 34. Each flow cell may correspond to one or more sample fields 36 on the sensing surface 34. Each flow cell may comprise at least one fluidic channel.

In embodiments where the different sample fields 36 may comprise different ligand molecules, the different sample fields 36 may be aligned with a corresponding fluidic channel having a corresponding ligand molecule. In embodiments where the reference sample comprises a separate sample solution, the microfluidic device may be configured to provide a reference sample. Alternatively, the reference sample may be provided separately without the use of the plurality of the flow cells. For example, each of the fluidic channels may be aligned to a particular sample field 28 such that one or more fluidic channels may be aligned to reference fields. In embodiments where the sample field corresponding to the reference sample is itself configured to function as a reference sample, the microfluidic device may not comprise a fluidic channel corresponding to the reference field.

Although not illustrated, a definer component may be provided to define the geometry and the number of sample fields 36. Also, the contrast between the sample fields 36 and their intermediate regions may be determined by the definer component. In certain embodiments, a definer component may be disposed in selected regions of the sensing surface 34. For example, the definer component may be disposed in regions around the sample fields 36. The regions having the definer component may not comprise the sample. In the case of SPR detection and imaging, the definer component may be used to create a contrast outside of surface plasmon resonance occurring in the SPR sensor surface areas (sample fields 36). The individual sample fields and the definer component surrounding the individual sensor fields are configured so that the reflectivity of the definer component is different than the reflectivity of the individual sample fields.

Simply, the definer component may be a patterned film of a suitable material. The definer component may include a light absorbing material. Suitable materials for the definer component may include layers of a light absorbing metal, or semiconductor, or polymer, such as photoresist polymers. In one embodiment, the sample fields 36 on the sensing surface 34 may be defined by the definer component. That is, the definer component in conjunction with the sensing surface 34 may define the sample fields 36 on the sensing surface 34. For example, the definer component may form continuous raised structures on the sensing surface 34, and areas enclosed by these raised structures may be defined as the sample fields 36. Positioning and adjusting the 2D array 30 of samples 32 may be done by selecting a suitable patterned film of the definer component. The creation of contrast enables the sample fields to be easily distinguished from non-sample fields' areas. In addition to distinguishing the areas of the sample fields 36 with the areas of the non-sample fields, the definer component may also minimize or prevent contamination between neighboring sample fields 36, or between the sample fields 36 and the sensing surface 34. For example, the definer component may form elevations above the sample fields in the direction perpendicular to the substrate. In case of water based sample solutions, it is desirable for the definer component to be hydrophobic or hydrophobicized so that an aqueous solution is well contained within the sample fields 36 without the possibility of cross-contamination with neighboring samples 32.

In addition to or in place of the definer component, a filtering component (not shown) may be used to filter off or absorb any light that is not reflected from the sample fields 36. For example, the filtering component may block the light (e.g., by absorbing the light) reflected from the areas around the sample fields 36. The blocking of the undesired light reduces the load at the detector, and enhances the performance of the device by reducing the noise. The filtering component may be disposed anywhere in the sample arm. In one embodiment, the filtering component may be disposed closer to the detector 66 than the sensing surface 34. In another embodiment, the filtering component may be disposed on the sensing surface 34. In one embodiment, the filtering component may be made of the same material as the definer component. The filtering component may have the similar shape/pattern as the definer component. In one embodiment, the filtering component and the definer component may be integrated to form one structure. In this embodiment, the integrated structure may be made of light absorption material.

The radiation source 12 provides a sample beam 40 that is directed towards the sample array 30 on the sensing surface 34 and interacts with the samples 32. The size of the sample beam may be large enough to cover the sample array 30. Alternatively, the beam 40 may be directed to a multi-spot generator optics to produce two or more spatially-spread discrete spots. In one example, the spatially-spread discrete spots are incident on a 2D array of samples. In one example, each of the spatially-spread discrete spots corresponds to a sample from the array of samples 32.

Although not shown, the optical engine 16 may also include other optical elements such as lens, filters, collimators, and the like. For example, a lens each may be disposed in the reference arm and the sample arm to direct the radiation to the detector.

The resultant sample radiation, generally referred to by the reference numeral 60, may be a reflective radiation or a transmissive radiation.

In certain embodiments, a phase difference may be introduced in the incident radiation 14 or resultant radiation 60 using a phase difference generator 62. The path length difference may be translated to phase difference in the interference spectrum. Resultant radiation 60 from the various detectable samples interfere with the resultant radiation from the reference sample and produces interference spectra. Introducing the phase difference provides a condition under which interference between the resultant beams from the reference and detectable samples may occur giving rise to intensity variations of the beam emerging from the sensing surface 34. The phase difference introduced in the incident radiation 14 or the resultant radiation 60 may be present in the interference spectra. The intensity of the beam received at the detector 66 may depends on the difference in the path length of the beams in the detectable and reference samples.

The phase difference generator 62 may introduce the phase difference between the incident sample beamlets and reference beamlets in the incident radiation 14. In certain other embodiments, the phase difference generator 62 may introduce a phase difference between the resultant beamlets reflected from the reference and detectable samples. In these embodiments, the resultant radiation 60 may be passed through a phase difference generator 62 before reaching the detector 66. The phase difference obtained between the reference and detectable samples may be used to spatially separate the various sample locations with respect to the spectral characteristics of the samples corresponding to those sample locations. In one example, the spectral characteristics for various sample locations may be reconstructed using Fourier transform.

The phase difference may be introduced in a first direction, and the imaging may be carried out in a second direction different from the first direction. Imaging in a direction different from that in which the phase difference is introduced, resolves the samples 32 in both first- and second-directions (e.g., x- and y-directions). In one example, the phase difference generator 62 may introduce a phase difference in an x-direction and the imaging may be done in a y-direction. In this example, the phase difference generator 62 facilitates resolving the samples 32 along the x-direction, and the detector resolves and spatially separates the samples 32 disposed along the y-direction.

In addition to the phase shift caused by the phase difference generator 62, the samples 32 disposed in the sample fields 36 may also contribute to the phase shift in the resultant sample radiation. The phase shift produced by the samples 32, may be a fraction of the phase shift produced by the phase shift generator 62. The small phase shift components contributed by the samples 32 may shift the corresponding fringes in the interference pattern. The shift of the fringes corresponds to the properties of the samples 32 at that sample fields 36. The additional shift in the resultant radiation caused by the samples 32 may be useful in determining the chemical or optical properties of the samples 32.

The imaging of the locations of the samples 32, for example a 2D array of samples, may be obtained by reconstructing absorption spectrum of the samples 32 using signal processing algorithms, such as but not limited to Fourier transform. Information regarding positions of the reference samples may be provided to the detector 66. The resultant radiation 60 comprising the sample and the reference resultant radiation may be separately identified by the detector 66. In certain embodiments, the samples 32 may be imaged in a single shot. The Fourier transform may be used to determine the spatially separated points (samples 32) from the acquired spectra without movement of any mechanical part or the reference beam, thereby improving the imaging speed.

The interference spectra between the resultant reference and sample radiation 60 may be analyzed and imaged using an imaging spectrometer 64. The imaging spectrometer 64 may include a spectrally separated detector 66 and a grating 68. The spectrally separated detector 66 may be a 2D detector. The spectral frequencies in the interference spectrum are separated using the detector 66 and the grating 68. The detector 66 detects a change in the optical properties of the reflected light from the 2D array of samples 32. The detector 66 may detect the analytes concentration, or chemical or biological composition in the sample.

The imaging spectrometer 64 may be operatively coupled to a signal processing unit 70 that measures interference spectra acquired by the detector 66. In the case of SPR detection and imaging, the wavelength sensitivity of the resonance may be used by maintaining the angle of incidence constant, and measuring the SPR effect as a function of wavelength. The reflectance spectrum exhibits a pronounced minimum due to the SPR effect in the visible to infrared wavelengths. In one embodiment, the position of the reflectance minimum shifts in wavelength upon the adsorption of sample molecules onto the metal surface due to the change of index of refraction at the sample-metal film interface. The detection system may be used to study the adsorption on a chemically modified metallic surface from the gas phase as well as from liquid solutions. In particular, the adsorption of biological molecules such as DNA, proteins, antibodies, and enzymes from aqueous solutions can be monitored in situ with the detection system. Advantageously, the detection system of the invention provides wavelength stability and measurement reproducibility, fast data acquisition rates and high signal-to-noise outputs, and broadened spectral range.

The imaging spectrometer 64 may be coupled to detection circuitry that may form part of the signal processing unit 70. In one example, the detection circuitry may convert current signal to voltage signal. Also, the detection circuitry may amplify the signal received from the imaging spectrometer 64. The detection circuitry may include components, such as but not limited to, data processor, for receiving measurements of interference pattern from the detector 66, such as a spectrometer, and for conducting analysis thereon, wherein the analysis comprises determining a parameter of an interference spectrum. Non-limiting examples of such parameters may include frequency, phase, and intensity of the interference fringes.

The detector 66 may be a photo-detector, a spectrometer, or a charge-coupled device (CCD), complementary metal oxide semiconductor (CMOS), a photodiode (such as an avalanche photodiode), solid state photomultiplier tube (PMT), image receptor, or a camera for measuring reflected light from the sample over a selected range of wavelengths. In embodiments where the detector 66 is a CCD or a camera, the detector 66 may record the spectrum of the reflected light from the sample. For each of the samples 32 on the sensing surface 34 there is a corresponding column or row in the 2D spectrometer to measure the interference spectrum of the corresponding sample on the sensing surface 34. If the imaging is done in a y-direction on the sensing surface 34 (which is e.g., a direction of columns), the different samples in a column are individually identified. However, for the samples 32 disposed in x-direction (which is e.g., a direction of rows) the different samples in a row are separately identified by introducing a phase difference using the phase difference generator 62. After imaging using the Fourier transform, the samples 32 in the 2D array of samples are individually identified by the detector.

A computer (not shown) may be used to process and display the signals and may form part of the signal processing unit 70. The computer may be used to generate a variety of quantitative and qualitative measures. For example, in quantitative measurements, the abscissa may represent time and the ordinate may represent percentage of concentration of an analyte. In addition, the computer may have a spectrum library, which stores the information regarding the spectral characteristics of various elements or chemical compounds. This spectrum library may be used to identify unknown samples by comparing the spectral information received from an unknown sample with spectral patterns retained in the library, and identification of the unknown substance may be made by comparison.

In one embodiment, an image stabilization unit (not shown) may be coupled to the optical engine 16 for stabilizing the image by countering, reducing or eliminating the environmental noise. For example, temperature stabilizing, or fringe locking the cavity may reduce or minimize the systematic noise like temperature noise, or mechanical noise. In another embodiment, the SNR may be improved by either integrating or averaging the signal over time. The SNR may also be improved by temperature stabilizing the sensing surface.

The detection and imaging system may be used in different detection techniques to obtain a one-shot/simultaneous detection for 1D or 2D array of samples. The sensing surface may be modified depending on the different applications. Also, other arrangement, such as relative position of the camera and the detector may be changed based on the application.

In certain embodiments, an SPR imaging system is provided for simultaneous detection and imaging of two or more samples. For example, the SPR imaging system may be used to detect a concentration of one or more analytes, such as biomolecules, or a rate of association and/or dissociation of one or more analytes in an analyte solution. In certain embodiments, an array of samples may be provided for simultaneous detection of concentration of two or more different analytes in a solution, or a concentration of a single analyte from two or more different analyte solutions. The multi-analyte format may also be used to detect the rate of reaction of the analytes in the solution. In one embodiment, the SPR imaging system comprises a broadband light source. In this embodiment, SPR curves in different wavelengths may be measured in a single shot image for the array of samples.

Figure 3:
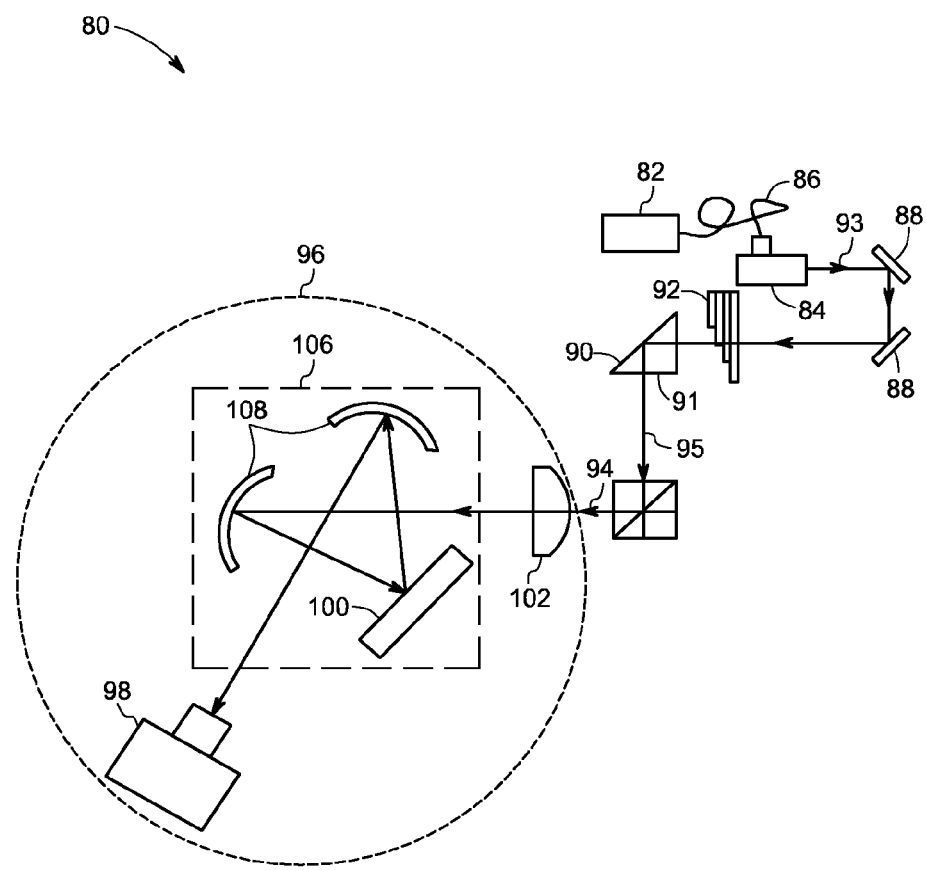
FIG. 3 is a schematic diagram of an example of a self-referencing surface plasmon resonance (SPR) detection and imaging system for simultaneous detection of an array of samples.

FIG. 3 illustrates an example of a SPR imaging system 80 for SPR detection and imaging of an array of samples (e.g., 2D array of samples). The system 80 comprises a broadband light source 82 for emitting broadband radiation. The radiation source 82 is optically coupled to the collimator 84 using an optical fiber 86. The collimated radiation or sample radiation 93 from the collimator 84 is directed to SPR sensing surface 90 using the mirrors 88. In one embodiment, the SPR sensing surface 90 may be made of a prism 91 coated with one or more thin metal films. The sensing surface 90 may comprise an array of sample fields. The array of sample fields may be used to dispose a plurality of samples including one or more reference samples. The incident radiation 93 undergoes internal reflection in the prism 91 and is reflected by the thin metal films and out of the sample fields on the sensing surface 90. The thin films may comprise metals, such as but not limited to, gold, silver or copper. The prism 91 may be made of glass, although various other materials having suitable optical properties for internally reflecting the incident beam 93 and transmitting the resultant reflected SPR beam 95 may also be used.

In one embodiment, a material of the definer component and the metal required for SPR phenomenon may be selectively disposed or patterned onto the sensing surface 90. That is, certain portions of the sensing surface 90 that are configured to receive the sample may include gold, while the other portions may not include gold, but may include the material of the definer component.

In one embodiment, a phase difference may be induced in the incident radiation 93 using a phase difference generator 92. Resultant radiation 95 from the various samples interferes with the resultant radiation from the reference sample and produces interference spectra 94. The interference spectra 94 are acquired by an imaging spectrometer 96. The spectrometer 96 comprises a detector 98, a grating 100 and one or more optical elements, such as a cylindrical lens 102.

The interference beam 94 passes through the cylindrical lens 102 and is received by the monochromator 124. In the illustrated embodiment, the monochromator 106 comprises cylindrical mirrors 108 and a grating 100. The reflected light from the monochromator 106 is received by the detector 98.

The interference beam 94 passes through the grating 100, which may split and diffract the interference spectrum into different wavelengths of light. The different wavelengths of light are then incident on the detector 98.

The SPR imaging system 80 may include a generally closed housing having an exit beam port therein to direct the beam at the imaging spectrometer 96. The broadband light source may be disposed within the housing, and the detector may be disposed outside the housing.

Figure 4:
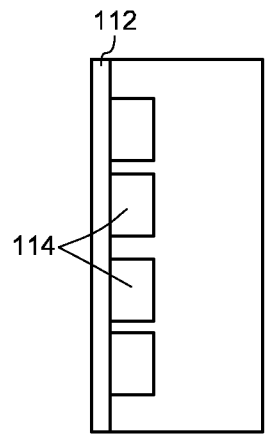
FIG. 4 is a cross-sectional view of an example of a sensing surface configured for free-solution SPR.

As illustrated in FIG. 4 the sensing surface 112 in the SPR may be configured for free-solution (label free) SPR. The sample fields 114 may be enclosed volumes (e.g., channels, cavities) that comprise one or more functionalizing agents, such as but not limited to, ligand molecules. One of the sample fields 114 may be configured to receive the sample solution, or act as a reference sample.

Figure 5:
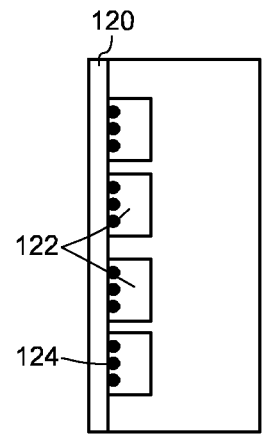
FIG. 5 is a cross-sectional view of an example of a sensing surface configured for localized SPR.

As illustrated in FIG. 5, the sensing surface 120 in the SPR may be configured for localized SPR (LSPR). The sample fields 122 may comprise electrically conductive structures 124 disposed at least in portions of the sample fields. One of the sample fields 122 may be configured to receive the sample solution, or act as a reference sample. Alternatively, the thin metal film, such as but not limited to, gold or silver, that is present to enable SPR phenomenon, may be patterned/textured to form the electrically conductive structures. In one embodiment, a patterned film may be used.

Resonance conditions of the LSPR may depend on the refractive index and dielectric constant surrounding the electrically conductive structures 124. The incident radiation interacts with the localized plasmons on surfaces of the electrically conductive structures 124. A change in the resonance conditions may be detected by measuring a change in the interference spectrum of the resultant projected to and transmitted through the electrically conductive structure of the sample fields. In one example, a biological reaction may cause a change in the dielectric constant of the electrically conductive structures 124, this change may be utilized for detection. In another example, an occurrence of an antigen-antibody reaction around the electrically conductive structure may be detected using the LSPR. In another embodiment, isolated particles may be disposed on the thin metal film Non-limiting examples of electrically conductive structures may include silver particles. The particles may be nanoparticles or microparticles.

Figure 6:
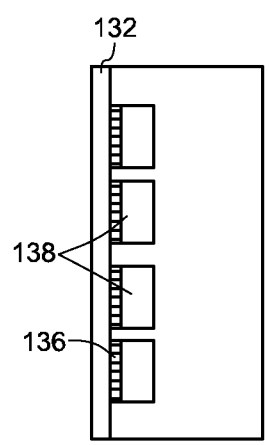
FIG. 6 is a cross-sectional view of an example of a sensing surface configured for nano-grating SPR.

FIG. 6 illustrates a nano-grating SPR arrangement comprising a transmitting substrate 132 (such as a glass substrate). The arrangement comprises a grating structure 136 disposed on the transmitting substrate 132. The grating structure 136 may be present in the form or a patterned film. Sample solutions may be disposed in sample fields 138 present on the sensing surface formed by the substrate 132 and the grating structure 136 to generate SPR phenomenon. One of the sample fields 138 may be configured to receive the sample solution, or act as a reference sample. Non-limiting examples of the detection film 134 may comprise a gold film, silver film, copper film, or combinations thereof. In one example, the grating structure may comprise a gold film disposed on a silver film. The grating structure 136 may include, but is not limited to, gold, silver, copper, or combinations thereof. The grating structure 136 may be a periodic metallic grating structure. In one embodiment, the grating structure 136 may comprise a spacing of between 50 and 500 nm between the gratings. The grating structure 136 may be fabricated using fabricating techniques, such as but not limited to, nano-imprinting technology, E-beam lithography, ultraviolet lithography, interference lithography, or other nanometric technologies, which are configured to achieve a nano-metric structures.

A shift of the wavelength for surface plasmon resonance may be used to detect biochemical molecules, and whereby a low-cost, compact and portable planar SPR detector is achieved. Advantageously, the nano-grating SPR may facilitate a low-cost, compact and portable planar surface plasmon resonance detector.

Although the methods and systems are discussed mainly with reference to SPR techniques, in one embodiment, the technique may be applied to a reflectometric interference spectroscopy (RIfS) to analyze a 2D array of samples. In this embodiment, a phase difference generator may be disposed in the beam path of either the resultant sample beam or a reference beam is a physical method based on the interference of broadband light at thin films, which may be used to investigate molecular interaction. RIfS, like SPR is a label-free technique, which allows the time-resolved observation of interaction among the binding partners without the use of fluorescence or radioactive labels.

Figure 7:
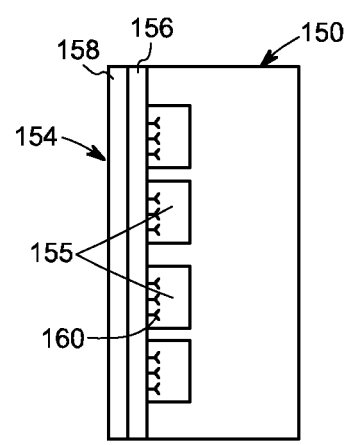
FIG. 7 is a cross-sectional view of an example of a sensing surface configured for reflectometric interference spectroscopy.

FIG. 7 illustrates an example where the self-referenced system employs a RIfS device 150. The device 150 comprises a sensing surface 154 having sample fields 155. The sensing surface 154 may comprise a multilayer structure 156 disposed on a transmitting substrate 158. In one example, the multilayer structure 156 comprises a plurality of layers. The various layers of the plurality of layers may comprise silica layers, high refractive index layers (such as but not limited to tantalum oxide layer). Beams incident on samples may be at least partially reflected and transmitted at phase boundaries formed between two adjacent layers of the multilayer structure 156. The reflected beams from the various samples may superimpose resulting in an interference spectrum. One or more samples may be configured to act as reference samples. In one embodiment, one or more layers of the multilayer structure 156 may be functionalized using functional agent 160 to facilitate interaction of a portion of the layer with target molecules. Interaction of the functionalized layers with the target molecules may provide a change in a thickness and the refractive index of the functionalized layers. Optical thickness is a product of physical thickness and refractive index, the optical thickness (pathlength) may be changed by changing the physical thickness and the refractive index of the layer. A change in the optical thickness of one or more layers of the plurality of layers may result in a modulation of the interference spectrum. Monitoring the modulation of the interference spectrum over time may be used to observe the binding behavior of the target molecules.

The arrangements illustrated in FIGS. 3-7 may be used in the optical engine 16 of FIGS. 1 and 2 to provide a self-referenced detection and imaging system. In these embodiments, one or more samples on the sensing surface may be reference samples. Phase differences may be introduced in a first direction that is different from an imaging direction to spectrally separate the samples in the first direction.

Figure 8:
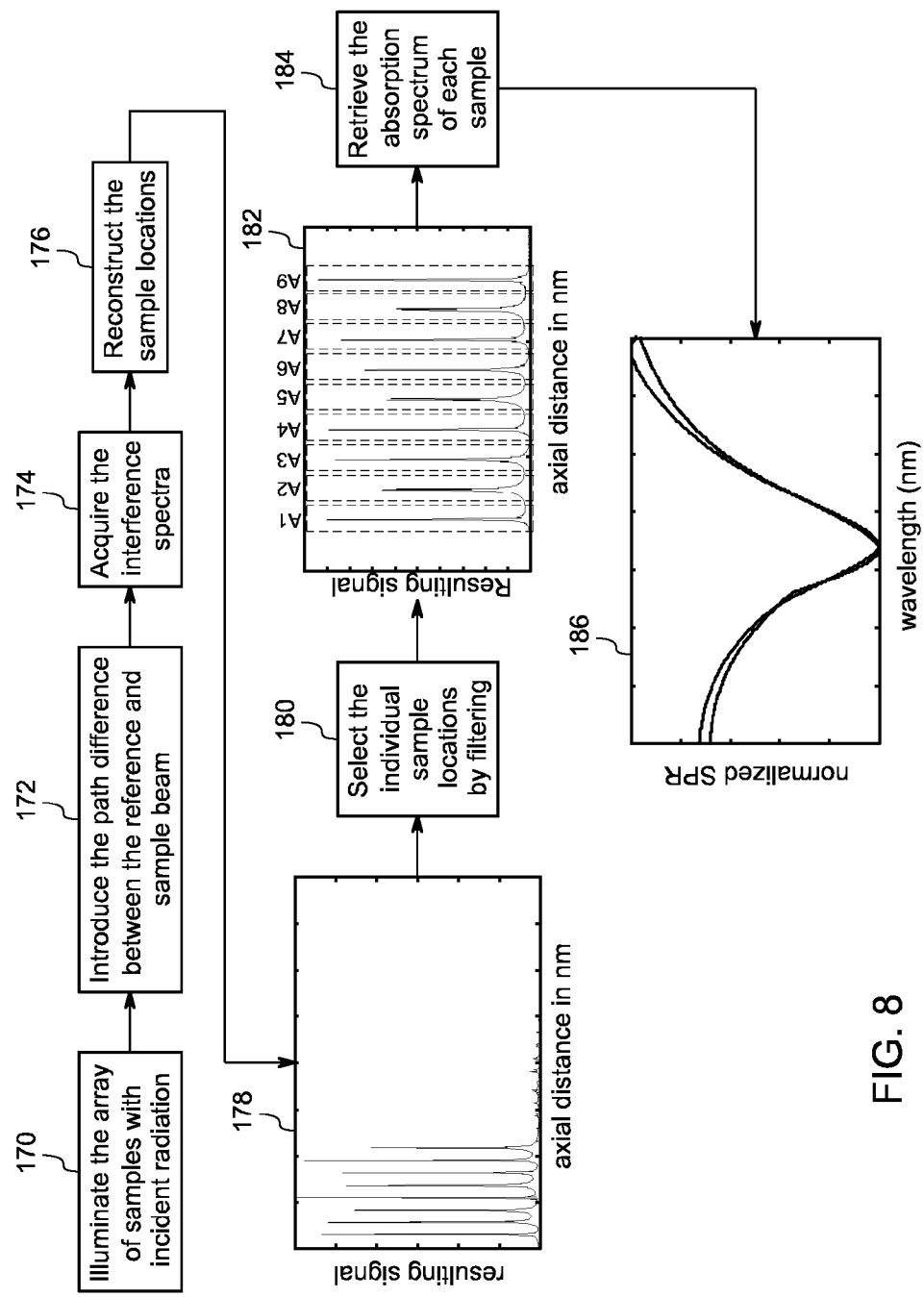
FIG. 8 is a flow chart of an example method for reconstructing an image of spectral characteristics for sample locations of the array of samples for self-referencing detection and imaging of an array of samples.

FIG. 8 illustrates an example of a method for simultaneous self-referenced detection of an array of samples. The method may be used for reconstructing images of spectral characteristics for samples in the array of samples. At step 170, the samples in the array of samples are illuminated with an incident radiation. The incident radiation may be provided by a single source, such as a broadband light source. The resultant sample beam from the samples may be a reflective or transmissive beam. At step 172, a path difference may be introduced in a first direction in the array of samples. The path difference may be introduced between beams paths of reference beams and sample beams. The path difference may be introduced in a direction that is perpendicular to a ruling direction of the grating of the spectrometer. Assuming that the direction of traversing the samples in a row is the first direction, which is also a direction perpendicular to the ruling direction of the grating. The phase difference generator may be disposed such that the portions of the phase difference generator having different paths are parallel to the first direction. In this way, the samples disposed in a particular row will have a path length difference induced in their corresponding incident beams or resultant reflected beams. An interference spectrum may be formed by interference of the sample beams with the reference beam. At step 174, interference spectra may be acquired. The interference spectra may be received by the detector. An spectral differences may be produced in the interference spectra by passing the interference spectra through a grating before receiving the spectra by the detector. In one example, the samples of a particular column may be spectrally resolved using a 2D detector. Steps 176-186 describe method steps for reconstructing spectral characteristics of samples from the acquired interference spectra. At step 176, an image of the array may be reconstructed using signal processing algorithms. In one example, the image of the array may be reconstructed using an inverse Fourier transform of the received interference spectra. The inverse Fourier transform may be computed to reconstruct sample locations (as illustrated by reference numeral 178). Advantageously, the different samples in the array are separately identifiable in the reconstructed image using the induced path length difference.

At step 180, filtering may be performed on the reconstructed image to separate the individual sample locations. The individual sample locations may be filtered depending on frequencies used by the individual samples. In one embodiment, as illustrated by reference numeral 182 a windowing technique may be used to separate the individual sample points. In another embodiment, the data may be analyzed using time frequency analysis to determine spectra and/or content of the different sample points. At step 184, the absorption spectrum of each sample may be retrieved. In one embodiment, a Fourier Transform may be applied to retrieve the frequencies corresponding to the different spatial locations of the samples. At step 186, the frequencies may be converted to wavelengths to determine the amount of absorption (e.g., SPR dip), or transmission.

Figure 9:
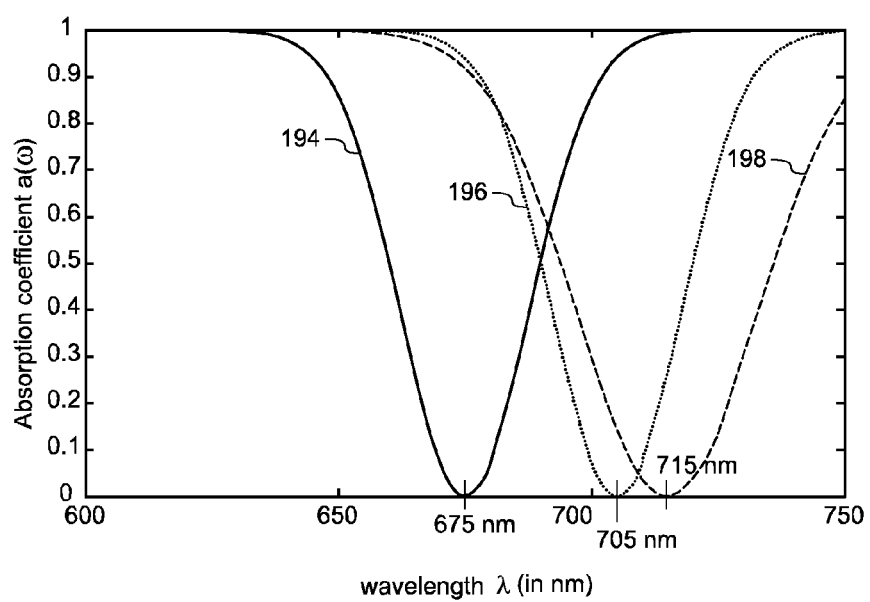
FIG. 9 is a graph of examples of simulation results for Gaussian profiles of absorption coefficients for three points on a sensing surface.
Figure 10:
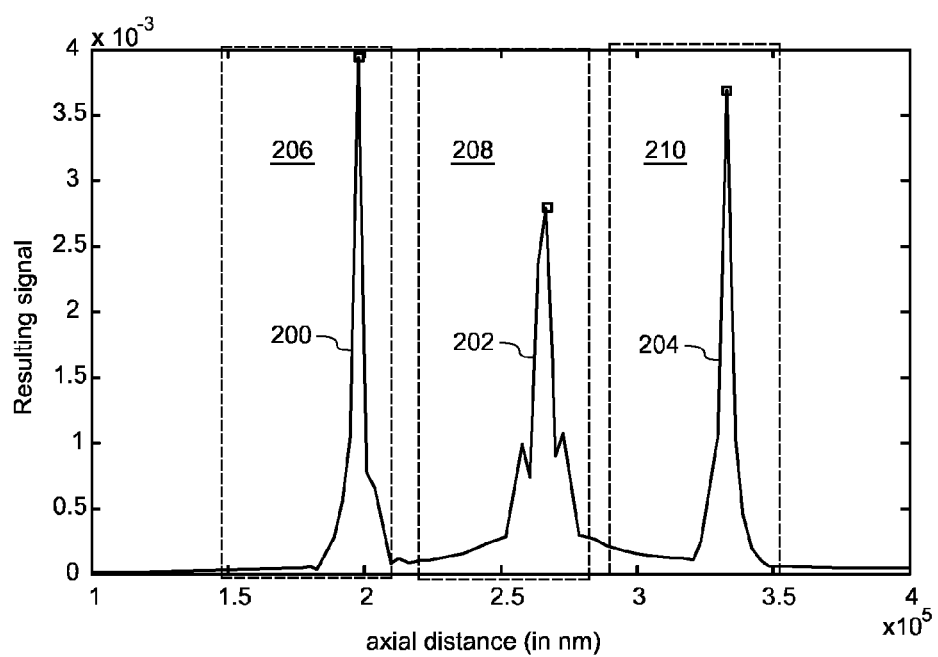
FIG. 10 are graphs corresponding to the three points of FIG. 11 for which inverse Fourier transform is calculated.
Figure 11:
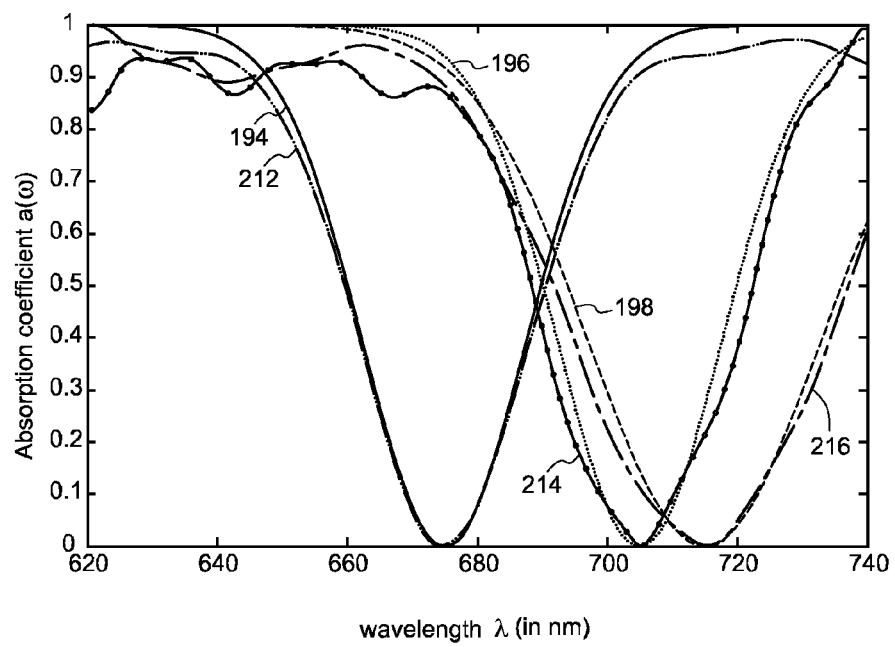
FIG. 11 are graphs for retrieved SPR for the three points of FIG. 10.

FIGS. 9-11 illustrate simulation results for image reconstruction for three points on a sensing surface. It is assumed that the samples at a first point and a second point have SPR phenomenon at 675 nm and 705 nm, respectively. It is further assumed that the third point is a buffer that has a SPR at 715 nm. A first point and a second point are at a distance of 0.0678 mm, and the first point and a third point are at a distance of 0.135 mm FIG. 9 illustrates Gaussian profiles of absorption coefficients for the three points, curve 194 represents the Gaussian profile for the first point, curve 196 represents the Gaussian profile for the second point, and curve 198 represents the Gaussian profile for the third point which is a buffer. The three curves show the dips at SPR wavelength. That is, for the first point (curve 194) the SPR dip is at 675 nm, for the second point (curve 196) the SPR dip is at 705 nm, and for the third point (curve 198) the SPR dip is at 715 nm. Using the numerical simulation and the signal processing approach, the retrieved spatial distance between samples or points is determined.

FIG. 10 illustrates curves 200, 202 and 204 that correspond to first, second and third points, respectively. The three dotted rectangles 206, 208 and 210 represent regions in the SPR curves 194, 196 and 198 (see FIG. 8) for which inverse Fourier transform is calculated. Spatial positions for the three points are retrieved by calculating the inverse Fourier transform. In one embodiment, a windowing technique may be performed to separate the spatial positions.

FIG. 11 shows the retrieved SPR for the three points. Once the three points are isolated (as shown in FIG. 8), a Fourier transform is performed to retrieve the frequencies corresponding to the three spatial positions. These frequencies are subsequently converted to wavelength in order to determine the SPR dip. In the illustrated embodiment, the retrieved SPR curves 212, 214 and 216 corresponding to the first, second and third point, respectively, on the sensing surface are shown in comparison with original SPR curves 194, 196 and 198. During processing, re-sampling of the data may be done to remove the nonlinearity in the data.

The systems and methods may be used in a variety of applications, for example, in molecular biology and medical diagnostics where specific binding of bioactive molecules to their corresponding binding partners, for example, DNA, proteins, need to be determined Based on the electrical detection of specific molecular binding events, the affinity sensor may be used to monitor, for example, molecules, viruses, bacteria, and cells in the most diverse samples, such as clinical samples, food samples, and environment samples such as, plants, whereby such monitoring is performed in a time efficient manner. The systems and methods may be used in the fields of molecular detection and concentration analysis of biomolecules, kinetic and equilibrium analysis of biochemical reactions, control of fermentation processes, evaluation of ligand-cell-interactions, clinical analysis, and cell demotion. The systems and methods may be used in determination of active concentration, screening and characterization in terms of both affinity and kinetics. Unlike fluorescence and chemiluminescence methods no dye-marked samples and also no antibodies are needed in SPR for the protein to be tested.

The systems and methods disclosed herein do not require repeating the methods steps for each sample of the plurality of samples and are configured to simultaneously detect (and image) a plurality of samples in the sample array. The methods do not require mechanical movement of parts of the systems for simultaneous detection of the plurality of samples. No mechanical movement facilitates longer lifetime of the instruments and provides relative immunity to the system from mechanical vibrations, which may be caused from moving instrument or instrument parts. In addition, self-referencing facilitates the use of a common path for the samples and references instead of two separate paths for the samples and references. Self-referencing the samples using one or more of the samples disposed on the sensing surface makes the system less prone to vibrations that may otherwise affect systems that employ separate sample and reference paths. Having one path in the interferometer instead of two, provides for a less complex and more robust system design while minimizing beam misalignment.

Large number of SPR curves for a sample array may be imaged in a single shot. The Fourier transform approach to 2D SPR provides enhanced signal-to-noise outputs, reproducibility, and spatial resolution. Processing plurality of samples (multiple spots) simultaneously in a single frame allows higher frame rates, thereby improving the signal-to-noise ratio. Advantageously, the monitoring or detection may be performed in real-time. The methods described and claimed may be used to analyze any binding reaction, including, but not limited to, those involving biological molecules. For antibody binding affinity measurements, an antigen typically is immobilized on the sensing surface. The sensing surface is exposed to a solution containing the antibody of interest, and binding proceeds. Once binding has occurred, the sensing surface is exposed to buffer solution (e.g. one that initially has no free antibody) and the dissociation rate is continuously monitored in real time.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A system for detecting an array of samples, comprising:
   an electromagnetic radiation source;
   a sensing surface comprising a two dimensional array having a plurality of rows in a x-direction and a plurality of columns in an orthogonal y-direction, wherein each row comprises a plurality of detectable sample fields each having a detectable sample disposed therein and at least one reference field each having a reference sample disposed therein, wherein a radiation resulting from the plurality of detectable sample fields and the at least one reference field arranged in each respective row interfere to form an interference spectra;
   a phase difference generator configured to introduce differences in path lengths of the radiation emitable from the electromagnetic radiation source incident on or resulting from the sensing surface, the phase difference generator introduces the phase difference between the detectable samples and the reference sample disposed in each respective row in the x direction; and
   an imaging spectrometer configured to acquire the interference spectra, wherein the imaging spectrometer is a 2D spectrometer comprising a detector and a grating element; and wherein for the detectable samples disposed in each respective row, the detector detects the phase difference introduced in the x direction of each respective row and the grating element is selected to spatially separate images of the detectable samples in the orthogonal y-direction.

2. The system of claim 1, wherein the reference sample comprises a determined spectral absorption.

3. The system of claim 1, wherein the reference sample comprises a material having a refractive index above a detectable range.

4. The system of claim 1, wherein the at least one reference field comprises one or more layers or coatings of metals or dielectric materials.

5. The system of claim 1, wherein the radiation resulting from the plurality of detectable sample fields and the at least one reference field share a common optical path.

6. The system of claim 1, wherein the sensing surface comprises two or more reference fields.

7. The system of claim 1, wherein each row or each column comprises a reference field specific to its respective row or column.

8. A system for detecting and imaging an array of samples, comprising:

a broadband light source configured to illuminate an array of samples;

an optical engine comprising:

a surface plasmon resonance sensing surface comprising a two dimensional array having a plurality of rows in a x-direction and a plurality of columns in an orthogonal y-direction, wherein each row comprises a plurality of detectable sample fields each having a detectable sample disposed therein and at least one reference field each having a reference sample disposed therein, wherein a radiation resulting from the plurality of detectable sample fields and the at least one reference field arranged in each respective row interfere to form an interference spectra;

a phase difference generator configured to introduce differences in pathlengths of the radiation emitable from the broadband light source incident on or resulting from the sensing surface, the phase difference generator introduces the phase difference between the detectable samples and the reference sample disposed in each respective row in the x-direction;

an image acquisition unit configured to acquire image data, the image data comprising the interference spectra; and a signal processing unit configured to process the acquired image data, wherein the image acquisition unit comprising a detector and a grating element, and for the detectable samples disposed in each respective row, the detector detects the phase difference introduced in the x-direction of each respective row and the grating element is configured to spatial separate images of the detectable samples in the orthogonal y-direction.

9. The system of claim 1, wherein the reference sample comprises a material having a refractive index below a detectable range.

10. The system of claim 1, wherein the interference spectra of the array of samples is collected simultaneously in a single frame.

11. A method for imaging samples in an array, comprising:

illuminating a sensing surface with an electromagnetic radiation source to generate respective resulting radiation, the sensing surface comprising a two dimensional array having a plurality of rows in a x-direction and a plurality of columns in an orthogonal y-direction, wherein each row comprises a plurality of detectable sample fields each having a detectable sample disposed therein and at least one reference field each having a reference sample disposed therein;

disposing a phase difference generator between the radiation source and the sensing surface;

introducing a pathlength difference in path lengths of the radiation emitable from the electromagnetic radiation incident on or resulting from the sensing surface;

interfering a radiation resulting from the plurality of sample fields and at least one reference field a radiation resulting from the plurality of detectable sample fields and the at least one reference field arranged in each respective row to form interference spectra;

acquiring the interference spectra; and reconstructing spectral characteristics of the plurality of detectable sample fields, wherein for the detectable samples disposed in each respective row, the acquiring step further comprises detecting the phase difference introduced in the x-direction of each respective row and spatially separating images of the detectable samples in the orthogonal y-direction.

* * * * *